United States Patent [19]

Dakubu

[11] Patent Number: 4,857,475
[45] Date of Patent: Aug. 15, 1989

[54] LABELLED AND LABELLABLE REAGENTS FOR FLUOROMETRIC ASSAYS
[75] Inventor: Salifu Dakubu, Winchester, Mass.
[73] Assignee: Roger Philip Ekins, United Kingdom; a part interest
[21] Appl. No.: 862,215
[22] PCT Filed: Aug. 22, 1985
[86] PCT No.: PCT/GB85/00377
§ 371 Date: Apr. 17, 1986
§ 102(e) Date: Apr. 17, 1986
[87] PCT Pub. No.: WO86/01604
PCT Pub. Date: Mar. 13, 1986
[30] Foreign Application Priority Data
Aug. 22, 1984 [GB] United Kingdom ............... 8421318
[51] Int. Cl.$^4$ .......................................... G01N 33/533
[52] U.S. Cl. ...................... 436/546; 436/500; 436/518; 436/537; 436/547; 436/805; 436/808; 530/390; 530/391; 530/405; 530/802; 534/16; 546/245; 546/249; 546/321
[58] Field of Search ............... 436/518, 537, 546, 547, 436/805, 808, 500; 546/245, 249, 321; 530/390, 391, 802, 405; 534/16

[56] References Cited
U.S. PATENT DOCUMENTS
3,956,341 5/1976 Loev .................................... 546/321
4,374,120 2/1983 Soini et al. ......................... 436/546

FOREIGN PATENT DOCUMENTS
2261767 9/1975 France .
2060623 5/1981 United Kingdom .

OTHER PUBLICATIONS
Jerry March, Advanced Organic Chemistry, 2nd Ed., pp. 816 & 722 (1980), McGraw-Hill, N.Y.
Chemical Abstracts, vol. 100, No. 188, 162q (1984), Ilkka et al–Europium as a Label in Time-Resolved Immunofluorometric Assays.
Clinical Chemistry–vol. 25, No. 3, pp. 353–361, Fluoroimmunoassay: Present Status and Key Problems–Soini et al.

Primary Examiner—Robert J. Warden
Assistant Examiner—Robert Benson
Attorney, Agent, or Firm—Steel, Gould & Fried

[57] ABSTRACT

Labellable reagents for fluormetric assays comprise a cyclic condensation product of a β-diketone, an aldehyde and an NH$_2$-bearing macromolecule, for example an antigen or antibody or a substance having an active group to which an antibody or antigen is linked. The reagents can chelate lanthanide metal ions such as Eu(II) and Tb(III) to form fluorescing complexes which can be used as labelled reagents for fluorometric assay of organic substances, for example antigens, antibodies and other substances occurring in body fluids.

9 Claims, 2 Drawing Sheets

LABELLED AND LABELLABLE REAGENTS FOR FLUOROMETRIC ASSAYS

TECHNICAL FIELD

This invention relates to the assaying of organic substances found in human and animal body fluids and the like. More particularly it relates to a fluorometric immunoassay and substances for use as labelled reagents in such an assay.

BACKGROUND ART

There are now a number of applications in which it is required to label antibodies (or other organic substances, for example macromolecules such as proteins, and haptens) with metal ions, either radioactive metal ions for use in radioimmunoassay and other nuclear medicine studies or lanthanide metal ions for fluorometric immunoassay and other studies involving fluorescence. For these purposes the organic substances are conventionally labelled with metal ions through the agency of chelates. Hitherto the chelates have been modified with bridging reagents which convert them into bifunctional reagents so that they retain their chelation function whilst being readily attachable by covalent bonding to the molecule to be labelled.

One class of chelating reagents which has been used for this purpose is the class of $\beta$-diketones, such as trifluoroacetylacetone and benzoyl and $\alpha$- and $\beta$-naphthoyl trifluoroacetone, and chelates of lanthanide metal ions with such reagents have been coupled to antibodies using EDTA-analogues (see European patent application No. 0.064,484). It has also been proposed in GB Patent Specification No. 1,560,402 to modify a $\beta$-diketone ligand such as thenoyl-trifluoroacetylacetone by the attachment of an aminomethyl substituent and to use one molecule of the modified ligand and two molecules of unmodified ligand to form a lanthanide metal ion complex which readily couples to an antibody after conversion of the amino group to an isothiocyanate group.

However, bifunctional-chelating agents are difficult to synthesize and many of the reactions by which covalent bonding of the ligand-metal ion complex to the molecule to be labelled is achieved have only a low yield of the desired labelled product and may also confer undesirable properties on the labelled molecule.

DISCLOSURE OF INVENTION

The present invention seeks to provide an alternative method of achieving satisfactory lining of a metal ion complex to an organic molecule and thereby conferring specialized functionality to the labelled molecule.

According to the present invention a method of potentiating an $NH_2$-bearing macromolecule for labelling with a metal ion comprises reacting the $NH_2$-bearing macromolecule with a $\beta$-diketone in the presence of an aldehyde to form a cyclic condensation product.

The invention also provides a method of potentiating an organic macromolecule for labelling with a metal ion, comprising reacting an $NH_2$-bearing compound having an active group capable of reaction with the organic macromole with a $\beta$-diketone in the presence of an aldehyde to form a cyclic condensation product and linking the resulting product to the organic macromolecule via the active group.

Further it provides a substance capable of being labelled with a metal ion for use in a fluorometric assay technique, comprising a cyclic condensation product of an $NH_2$-bearing macromolecule, a $\beta$-diketone and an aldehyde.

It also provides a labelled reagent for use in fluorometric assay comprising a cyclic condensation product of an aldehyde, a $\beta$-diketone and an organic substance having an $NH_2$ group, the condensation product being chelated to a lanthanide metal ion to form a complex capable of being estimated fluorometrically, and a process for the fluorometric assay of an organic substance in which such a labelled reagent is used.

BRIEF DESCRIPTION OF THE DRAWINGS

The invention is illustrated by the accompanying drawings which are graphs relating to assays of alphafa-eto-protein (selected as using a typical $NH_2$-containing antibody), as described in the Examples below.

DETAILED DESCRIPTION OF THE INVENTION

Figure 1:
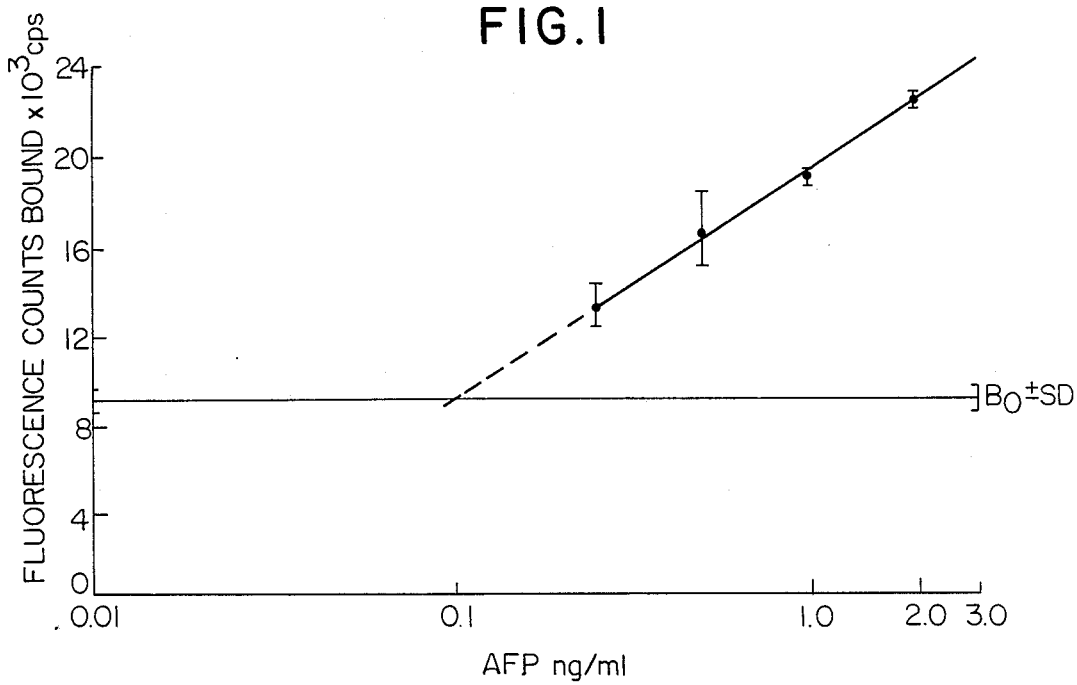
FIG. 1 is a calibration curve using rabbit and anti-alpha-faeto-protein (AFP) directly labelled with trifluoroacetylacetone.
Figure 2:
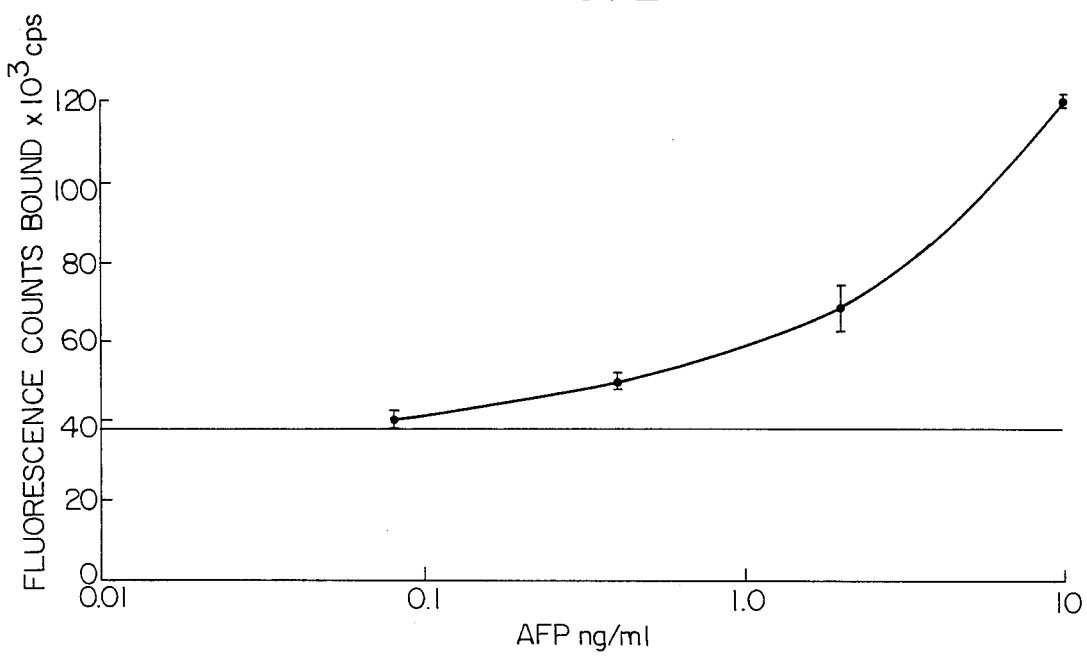
FIG. 2 is a calibration curve in which the anti-AFP has been labelled using labelled polylysine.
Figure 3:
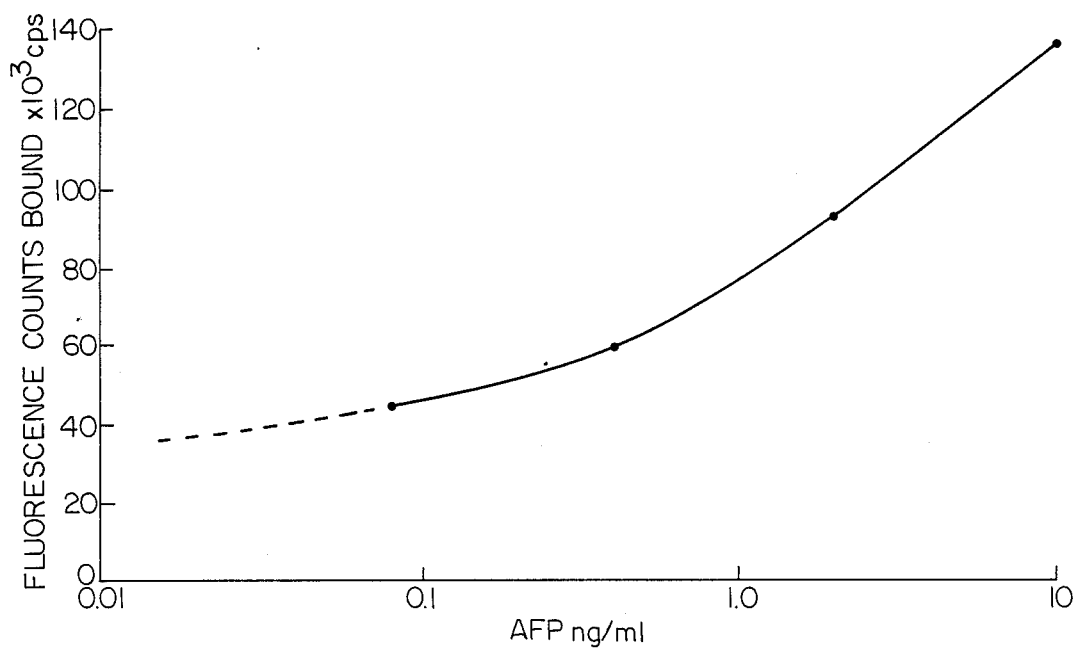
FIG. 3 is the calibration curve shown in FIG. 2 when Eu(III) fluorescence was fully enhanced.

The reaction between the $NH_2$-bearing substance or macromolecule ($R^1$—$NH_2$), the $\beta$-diketone ($R^3COCH_2COR^3$) and the aldehyde ($R^2$—$CHO$) to form the cyclic condensation product can be represented by the following equation:

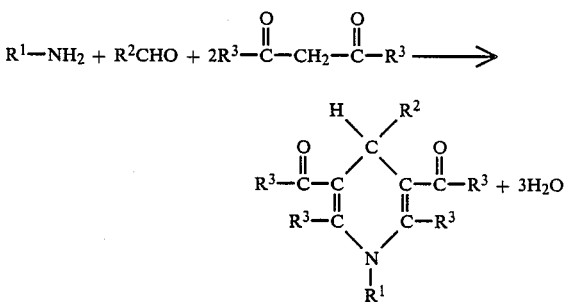

The sumbols $R^1, R^2$ and $R^3$ are arbitrary symbols dependent on the nature of the starting materials.

The method of the invention does not require the prior modification of the $\beta$-diketone and, because it depends only on the basic structure of the $\beta$-diketone and not on the nature of any substituents, it can be used with a wide variety of different $\beta$-diketones. It is therefore possible to choose the optimum $\beta$-diketone on the basis of other criteria, for example formation of soluble complexes having satisfactory absorption spectra and formation constants with a metal ion introduced for labelling purposes without loss of immuno reactivity or for the avoidance of toxic effects. $\beta$-Diketones which have been used successfully include both aromatic and non-aromatic species, and it is preferred to employ a fluorine-substitued material when producing a complex for labelling with a lanthanide metal ion for fluorometric purposes. Examples of suitable $\beta$-diketones are trifluoroacetylacetone, thenoyltrifluoroacetone, 4,4,4-trifluoro-1,(2-furyl)1,3-butanedione and $\beta$- and $\beta$-naphthoyltrifluroacetone. Other suitable $\beta$-diketones are those mentioned in an article by Hemmila et al in Analytical Biochemistry, 137, 335–343 (1984) or in UK Patent Specification No. 1560402 or European Patent Application No. 0,064,484 mentioned above or in European Patent Application No. 0,002,963.

It may be advantageous to employ the β-diketone in the form of a metallic β-diketonate with the metal of interest or with another metal (for example with copper) in order to promote the chelation properties of the final product. If the initial metal is not the metal of interest it can then be displaced with the metal of interest, for example a lanthanide metal, to form the labelled product.

The aldehyde used is preferably formaldehyde when specialized functionality, e.g. chelation, is not required in the aldehyde, but other aldehydes may be used if desired, for example $C_1$–$C_4$-alkylaldehydes optionally bearing inert substituents, and this gives a further means of varying the properties of the resulting cyclic condensation product. The aldehyde itself may have chelating properties deliberately built into its chemical structure and these will then assist in the chelation of the metal in the labelled product.

The invention can be used to provide labelled reagents, and precursors therefor, from organic substances whether they initially contain sufficient $NH_2$ groups for the formation of the cyclic condensation product or not. Where the organic substance contains no or insufficient $NH_2$ groups initially, a cyclic condensation product may be formed by initial reaction of the β-diketone and the aldehyde using an amine or amino acid or other $NH_2$-containing compound, for example an $NH_2$-containing polymer (such as a polylysine), having an active group capable of reacting with the macromolecule. The resulting cyclic condensation product is then reacted with the organic substance to be labelled by a mild reaction through the active group to attach it to the organic substance. An example of such a reaction is the carbodiimide reaction. Alternatively, an active ester can be made, for example the hydroxysuccinimide active ester of poly-L-lysine. Instead of the polylysine it is possible to use a lysine-containing chelate, which will then provide further assistance in chelating the metal in the final product. An example of such a chelate is siderophilin (transferrin).

The invention may thus be used to potentiate for labelling with metal ions a wide variety of organic substances naturally occurring in human and animal body fluids or cultivated or generated artificially, for example antigens, antibodies, hormones (e.g. T4), enzymes and other proteins and haptens, and all such substances are intended to be encompassed within the term organic macromolecule as used herein. The substances in question will in general have molecular weights in excess of 300 in order to qualify as macromolecules, but substances of lower molecular weight are not excluded. The macromolecule will in general contain linked subunits such as amino acid residues but this is not a requirement.

The reaction to form the cyclic condensation product is preferably carried out at a mildly acid pH, for example 5.5 to 6.5, although alkaline pHs are not ruled out. Preferably it is carried out at a mildly elevated temperature, for example 30°–50° C. The use of high temperatures which would damage the $NH_2$-bearing macromolecule is to be avoided when manufacturing the condensation product for use in a subsequent assay. The use of lower temperatures will reduce the rate of reaction and a prolonged incubation period may be required.

Cyclic condensation products according to the invention are stable and strongly chelate metal ions such as lanthanide metal ions. Thus, they may be reacted to form a complex of Eu(III) or other lanthanide metal such as Tb(III) capable of giving fluorescent complexes and the resulting complex will in general be fluorescent in solution without the need to add exogenous β-diketone. The reaction may be carried out in any known or conventional manner, for example by dialysis against a buffer containing ions of the metal to be incorporated.

The condensation products produced with chelating aldehydes satisfy the coordination capacity of the lanthanide metals more completely than the products from other aldehydes. Such products therefore chelate metals better and are more fluorescent when in the form of lanthanide chelates.

The absorption maximum wave lengths of the condensation products are usually slightly shifted either way, depending on the starting β-diketone, from that of the β-diketone. This shift in wave length and hence excitation maximum may be used as an index of the formation of the condensation product.

The cyclic condensation product labelled with a lanthanide metal ion may be used as a labelled reagent in the fluorometric assay of a wide variety of substances but it is primarily intended for the estimation of organic macromolecules and haptens occurring in body fluids either naturally or as a result of disease or malfunction or the treatment of disease or malfunction, for example antibodies, antigens and other proteins, hormones, enzymes, drugs and viral particles. The fluorometric assay may be carried out using any known or standard techniques. Examples of suitable techniques are mentioned in the patent specifications and applications referred to above and in the references mentioned in them. See also Dakubu S., Ekins R. P. et al, "High-sensitivity, pulsed-light time-resolved fluoroimmunoassay" in Practical Immunoassay, W. Butt (Ed)., Marcel Dekker Inc., pages 71–101. The assay may be a qualitative assay, used purely for detection of a possible antibody or other substance, or a quantitative assay, used to estimate the concentration of the substance to be assayed.

One preferred assay procedure is a two-site (sandwich) procedure in which the substance to be assayed (e.g. an antibody or antigen) is reacted initially with its complement (e.g. an antigen therefor or an antibody therefor), suitably whilst the latter is attached to a solid substrate, and the product reacted with a labelled reagent capable of interacting with the bound substance being assayed (e.g. labelled antigen or labelled antibody).

An alternative fluorometric assay involves a methodology akin to a standard radioimmunoassay in which the substance to be assayed (e.g. an antigen or antibody) and a labelled reagent compete for reactive sites on a complement (e.g. an antibody or antigen) which is conveniently attached to a solid substrate.

When the cyclic condensation product is being used in a fluorometric immunoassay it is possible to carry out the measurement of fluorescence for the determination of the lanthanide metal ion (e.g. Eu(III)) either in solution or when the labelled molecule is attached to a solid support. When the measurement is being carried out in solution the lanthanide metal ion can be extracted from the labelled complex, for example by reaction with added β-diketone (which need not be the same as the β-diketone used to form the complex). The added β-diketone complexes with the metal ion and thereby displaces the condensation product, and the resulting complex can be separated from the condensation product. However, it is an advantage of the present invention that it is not necessary to use such an enhancement solution for the measurement of the fluorescence but that the complex of the condensation product with the lanthanide metal ion is inherently fluorescent so that its fluorescence can be measured directly whilst it is still bound to the reaction product.

For determination of the amount of fluorescence in solid form or in solution improved results may be obtained by addition of trioctylphosphine oxide (TOPO), as mentioned in European Patent Application No. 0,064,484. This enables the labelled macromolecule to be determined fluorometrically to better than $10^{-10}M$ concentration.

The cyclic condensation product, suitably in solution in a buffer, may thus form part of a kit for carrying out fluorometric assays, the organic substance participating in the condensation product (either directly or by subsequent reaction with an active group of the $NH_2$-bearing substance actually participating) being chosen appropriately depending on the substance being assayed so as to be capable of interacting either with the substance to be assayed or with its complement, for example a suitable antibody or antigen. The kit conveniently includes the ready-chelated complex of a lanthanide metal ion such as Eu (III) or Tb (III) with the condensation product. The kit may also include as a separate component a complement for the substance to be assayed, that complement being bound on a solid support.

MODES FOR CARRYING OUT THE INVENTION

The following reagents were used in the following examples which are presented for illustrative purposes only and are not intended to limit the scope of the invention.

(1) A commercially available rabbit anti-AFP solution containing approximately 1 mg/ml.
(2) A 1:10 dilution of a formaldehyde solution originally 37–40% w/v in formaldehyde, thus now having a concentration of about $1.4 \times 10^{-3}$ moles/liter.
(3) A stock solution of cupric trifluoroacetylacetone (CuTFAA) in methanol at a concentration of 160 mM.

EXAMPLE 1

400 μl of the anti-AFP solution (i.e. $2.7 \times 10^{-8}$ mole of anti-AFP) were incubated at 37° C. for 1 hour with 200 μl of the diluted formaldehyde solution (i.e. $2.7 \times 10^{-7}$ mole of formaldehyde) and 4 μl of the Cu TFAA solution (i.e. $5.4 \times 10^{-7}$ mole of Cu TFAA) in an acetate buffer (0.2M) at a pH of 5.7. The reaction product was dialysed initially against the acetate buffer to remove unreacted small molecules then against the acetate buffer containing Eu(III) ions at $10^{-7}M$ concentration to form the chelation product (labelled antibody), and finally against the acetate buffer to remove excess Eu(III). The labelled antibody was dissolved in a tris(hydroxymethyl) aminomethane/saline/azide buffer (0.02M) at a pH of 7.6 (50 mM in NaCl) for assay purposes. If desired, it could have been further purified by chromatography.

EXAMPLE 2

The above procedure was repeated using, in place of the rabbit anti-AFP, a polylysine of molecular weight 80,000. The resulting labelled polylysine was coupled to antibody using 1-ethyl-3 (3-dimethylaminopropyl-carbodiimide hydrochloride.

The labelled products obtained in Examples 1 and 2 were used in assays for AFP by a standard two-site ("sandwich") assay procedure.

I claim:

1. A substance capable of being labelled with a metal ion for use in a fluorometric assay technique, comprising a cyclic condensation product of an $NH_2$-bearing macromolecule, a β-diketone and an aldehyde and having the formula:

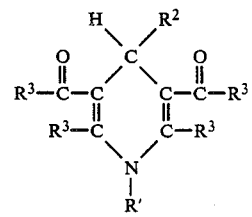

where R'N is the residue of an antibody or antigen of the formula $R'NH_2$ or R'N is the residue remaining after subtraction of two hydrogen atoms of an $NH_2$ group from an $NH_2$ containing compound covalently bonded to an antibody or antigen or R'N is the residue of a polylysine of the formula $R'NH_2$ having a functional group through which it can be covalently bonded to an antibody or antigen; $R^2$ is hydrogen or alkyl of 1 to 4 carbon atoms derived from formaldehyde or a $C_1$-$C_4$-alkylaldehyde and the moieties

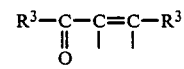

are residues of β-diketones of the formula

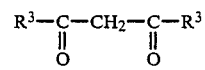

selected from the group consisting of trifluoroacetylacetone, thenoyltrifluoroacetone, 4,4,4-trifluoro-1(2-furyl)-1,3-butanedione, α-naphthoyltrifluoroacetone, benzoylacetone, dibenzoylmethane, β-naphthoyl-2-furoylmethane, di(p-fluorobenzoyl)methane, hexafluoroacetylacetone, benzoyltrifluoroacetone, p-methoxybenzoyltrifluoroacetone, p-fluorobenzoyltrifluoroacetone and dithenoylmethane.

2. A substance as claimed in claim 1 wherein the β-diketone is selected from the group consisting of trifluoroacetylacetone, thenoyltrifluoroacetone, 4,4,4-trifluoro-1(2-furyl)-1,3-butanedione and α- and β-naphthoyltrifluoroacetone.

3. A substance as claimed in claim 1 wherein $R^2$ is hydrogen derived from formaldehyde.

4. A substance as claimed in claim 1 wherein R'N is the residue of a compound of the formula $R'NH_2$ selected from anti-alpha fetoprotein, polylysine, thyroxine and siderophillin.

5. A labelled reagent for use in the fluorometric assay of am analyte comprising a cyclic condensation product of an aldehyde, a β-diketone and an organic substance having an NH₂ group, the condensation product having the formula:

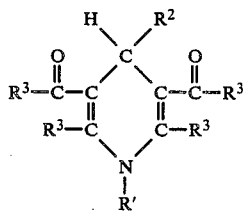

where R'N is the residue of an antibody or antigen of the formula R'NH₂ capable of binding specifically with the analyte to be assayed or R'N is the residue remaining after subtraction of two hydrogen atoms of an NH₂ group from an NH₂-containing compound covalently bonded to an antibody or antigen capable of binding specifically with the analyte to be assayed, R² is hydrogen or alkyl of 1 to 4 carbon atoms from formaldehyde or a C₁-C₄-alkylaldehyde and the moieties

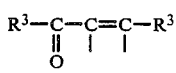

are residues of β-diketones of the formula

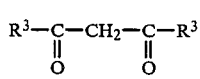

selected from the group consisting of trifluoroacetylacetone, thenoyltrifluoroacetone, 4,4,4-trifluoro-1(2-furyl)-1,3-butanedione, α-naphthoyltrifluoroacetone, benzoylacetone, dibenzoylmethane, β-naphthoyl-2-furoylmethane, di(p-fluorobenzoyl)methane, hexafluoroacetone, benzoyltrifluoroacetone, p-methoxybenzyltrifluoroacetone, p-fluorobenzoyltrifluoroacetone and diethenoylmethane; the condensation product being chelated to lanthanide metal ion to form a complex capable of being detected fluorometrically.

6. A labelled reagent as claimed in claim 5 wherein R'N is the residue remaining after subtraction of two hydrogen atoms of an NH₂ group from a polylysine covalently bonded to an antigen or antibody.

7. A labelled reagent as claimed in claim 5 wherein the lanthanide metal ion is europium (III) or terbium (III).

8. A kit for use in the fluorometric assay of an antigen comprising a buffered solution of a cyclic condensation product of an aldehyde, a β-diketone and an organic substance having an NH₂ group, the condensation product having the formula:

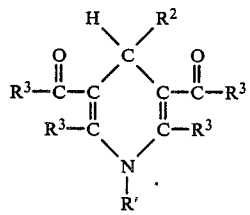

where R'N is the residue of an antibody of the formula R'NH₂ which is an antibody to the antigen to be assayed or R'N is the residue remaining after subtraction of two hydrogen atoms of an NH₂ group from an NH₂-containing compound covalently bonded to an antibody to the antigen to be assayed, R² is hydrogen or C₁-C₄-alkyl derived from formaldehyde or a C₁-C₄-alkylaldehyde and the moieties

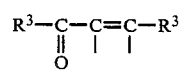

are residues of β-diketones of the formula

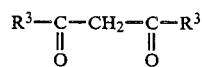

selected from the group consisting of trifluoroacetylacetone, thenoyltrifluoroacetone, 4,4,4-trifluoro-1(2-furyl)-1,3-butanedione, α-naphthoyltrifluoroacetone, β-naphthoyltrifluoroacetone, benzoylacetone, dibenzoylmethane, β-naphthoyl-2-furoylmethane, di(p-fluorobenzoyl)methane, hexafluoroacetylacetone, benzoyltrifluoroacetone, p-methoxybenzoyltrifluoroacetone, p-fluorobenzoyltrifluoroacetone and dithenoylmethane, the condensation product being chelated to a lanthanide metal ion to form a complex capable of being detected fluorometrically.

9. A kit as claimed in claim 8 wherein the lanthanide metal ion is europium (III) or terbium (III).

* * * * *